(12) United States Patent
Habel et al.

(10) Patent No.: US 10,343,224 B2
(45) Date of Patent: Jul. 9, 2019

(54) INTERPOLATED MILLING TOOLS AND METHODS

(71) Applicant: Ford Motor Company, Dearborn, MI (US)

(72) Inventors: Michael Joseph Habel, Ann Arbor, MI (US); Gregory S. Carlone, Novi, MI (US); Emenike Nick Chukwuma, Westland, MI (US); Youssef Ziada, Milford, MI (US)

(73) Assignee: Ford Motor Company, Dearborn, MI (US)

( * ) Notice: Subject to any disclaimer, the term of this patent is extended or adjusted under 35 U.S.C. 154(b) by 0 days.

(21) Appl. No.: 15/090,101

(22) Filed: Apr. 4, 2016

(65) Prior Publication Data

US 2017/0282259 A1 Oct. 5, 2017

(51) Int. Cl.
*B23C 3/28* (2006.01)
*B23C 3/05* (2006.01)
(Continued)

(52) U.S. Cl.
CPC ............... *B23C 3/05* (2013.01); *B23C 3/28* (2013.01); *B23C 3/34* (2013.01); *B23C 5/10* (2013.01);
(Continued)

(58) Field of Classification Search
CPC .... B23C 3/05; B23C 3/28; B23C 5/10; B23C 2210/247; B23C 2210/287; B23C 3/34
See application file for complete search history.

(56) References Cited

U.S. PATENT DOCUMENTS

| | | | |
|---|---|---|---|
| 582,081 A * | 5/1897 | Newton | B23B 27/10 407/11 |
| 2,431,294 A * | 11/1947 | Dulmage | B23C 7/00 241/279 |

(Continued)

FOREIGN PATENT DOCUMENTS

| | | | | |
|---|---|---|---|---|
| CA | 1115038 A | * | 12/1981 | ............. B27G 13/14 |
| DE | 3024186 A1 | * | 1/1982 | ........... B23C 5/2265 |

(Continued)

OTHER PUBLICATIONS

EPO Machine translation of DE 3707146, printed Aug. 2017.*
(Continued)

*Primary Examiner* — Daniel W Howell
(74) *Attorney, Agent, or Firm* — Ray Coppiellie; Brooks Kushman P.C.

(57) ABSTRACT

Milling tools and methods are disclosed. The method may include moving a milling tool having at least two axially spaced apart sets of cutting inserts to an axial position within a bore in a material and rotating the milling tool about a longitudinal axis. Contact between the milling tool and a wall of the bore may be initiated in a region of the wall having a least amount of material at the axial position. The milling tool may include a tool shaft having a longitudinal axis, a first set of radially spaced cutting inserts coupled to the tool shaft, and a directly adjacent second set of radially spaced cutting inserts coupled to the tool shaft and spaced from the first set of cutting inserts along the longitudinal axis. The first and second sets of cutting inserts may be staggered from each other by at least 10 degrees.

18 Claims, 6 Drawing Sheets

(51) Int. Cl.
*B23C 5/10* (2006.01)
*B23Q 11/10* (2006.01)
*G01N 3/30* (2006.01)
*B23C 3/34* (2006.01)

(52) U.S. Cl.
CPC .......... *B23Q 11/1046* (2013.01); *G01N 3/30* (2013.01); *B23C 2210/247* (2013.01); *B23C 2210/287* (2013.01); *B23C 2220/04* (2013.01); *B23C 2220/36* (2013.01); *B23C 2250/12* (2013.01)

(56) References Cited

U.S. PATENT DOCUMENTS

| | | | | |
|---|---|---|---|---|
| 2,965,143 | A * | 12/1960 | Feldmann | B27B 33/12 407/61 |
| 3,237,275 | A * | 3/1966 | Middleton | B23C 5/2269 144/229 |
| 3,986,543 | A * | 10/1976 | Slayton | B27G 13/005 144/236 |
| 4,411,563 | A * | 10/1983 | Moon | B23B 51/02 407/54 |
| 4,443,136 | A * | 4/1984 | Kemmer | B23B 27/083 407/110 |
| 4,674,923 | A * | 6/1987 | Ogilvie | B23C 5/12 144/237 |
| 4,681,485 | A | 7/1987 | Koelewijn | |
| 4,847,961 | A * | 7/1989 | Donovan | B23B 29/03446 29/26 A |
| 4,936,717 | A * | 6/1990 | Bosek | B23C 5/08 144/218 |
| 5,017,055 | A * | 5/1991 | Tsujimura | B23C 5/1045 407/113 |
| 5,876,155 | A | 3/1999 | Link et al. | |
| 6,343,902 | B1 * | 2/2002 | Nishikawa | B23C 3/02 407/31 |
| 6,371,702 | B1 * | 4/2002 | DeWald, Jr. | B23B 51/0009 408/227 |
| 7,399,146 | B2 | 7/2008 | Long, II et al. | |
| 8,555,503 | B2 | 10/2013 | Habel et al. | |
| 8,714,890 | B2 * | 5/2014 | Davancens | B23B 35/00 407/118 |
| 8,807,881 | B2 | 8/2014 | Itoh et al. | |
| 2004/0013477 | A1 * | 1/2004 | Helvey | B23C 5/1054 407/30 |
| 2008/0170917 | A1 * | 7/2008 | Hilker | B23C 5/1054 407/54 |
| 2012/0328820 | A1 * | 12/2012 | Goehlich | B29C 65/5035 428/58 |
| 2013/0272807 | A1 * | 10/2013 | Luik | B23C 5/109 407/11 |

FOREIGN PATENT DOCUMENTS

| | | | | |
|---|---|---|---|---|
| DE | 3104752 A1 * | 8/1982 | | B23C 5/28 |
| DE | 3707146 C1 * | 11/1987 | | B23C 3/34 |
| DE | 10011113 A1 * | 9/2001 | | B23B 29/02 |
| DE | 20201144 U1 * | 6/2002 | | B23C 5/08 |
| DE | 102005034426 A1 * | 12/2006 | | B23B 27/007 |
| DE | 102007030876 A1 * | 1/2009 | | B23C 5/2413 |
| DE | 102011055210 A1 * | 5/2013 | | B23G 5/18 |
| EP | 0628369 A1 * | 12/1994 | | B23C 5/1081 |
| JP | 2001334408 A | * 12/2001 | | |
| JP | 2002066830 A | * 3/2002 | | |
| JP | 2010149220 A | * 7/2010 | | |
| JP | 2013111709 A | * 6/2013 | | |
| JP | 2013154415 A | * 8/2013 | | |

OTHER PUBLICATIONS

Palpandian, P. et al., "Stability Lobe Diagram for High Speed Machining Processes: Comparison of Experimental and Analytical Methods—A Review," Int'l J. of Innovative Research in Science, Engineering and Technology, v. 2, Issue 3, Mar. 2013, pp. 747-752.

Yue, J., "Creating a Stability Lobe Diagram," Proceedings of the 2006 IJME—Intertech Conference (2006), 18 pgs.

* cited by examiner

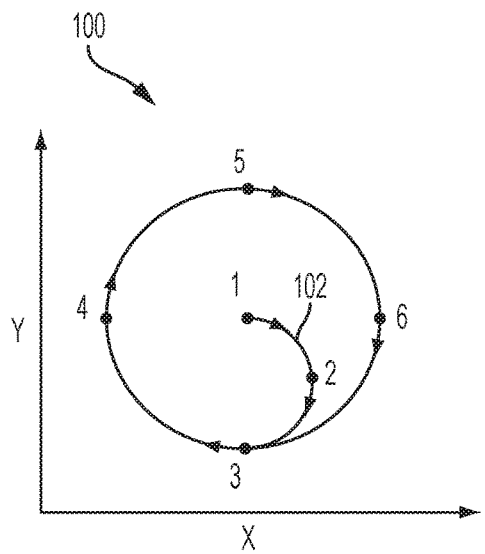
FIG. 11
| POINT ID | X | Y | Z |
|---|---|---|---|
| 1 | 0 | 0 | -42.5 |
| 2 | 1.125 | -1.125 | -42.5 |
| 3 | 0 | -2.25 | -42.5 |
| 4 | -2.25 | 0 | -42.5 |
| 5 | 0 | 2.25 | -42.5 |
| 6 | 2.25 | 0 | -42.5 |
FIG. 12
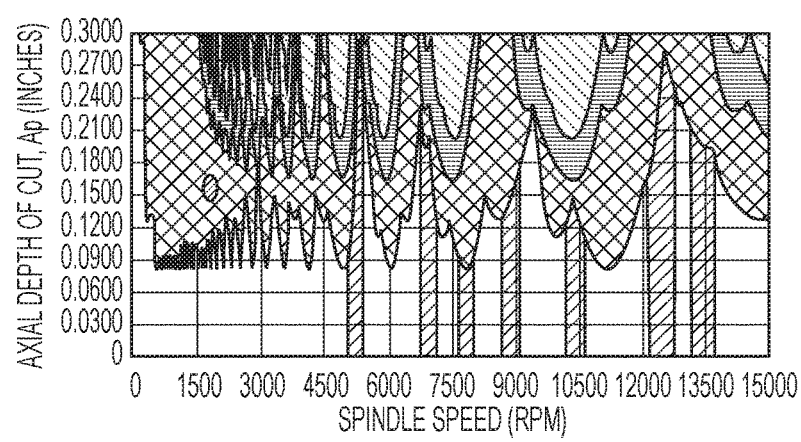
FIG. 13

INTERPOLATED MILLING TOOLS AND METHODS

TECHNICAL FIELD

The present disclosure relates to interpolated milling tools and methods, for example, for milling grooves and/or faces in a valve body.

BACKGROUND

Valves are used in numerous applications, including automotive applications. One example may be in an automatic transmission, which may include a hydraulic system for regulating fluid pressure and hydraulic fluid flow in various lines connected to components of the transmission. The system may include a regulator spool valve packaged in a main control casting. The casting, which may be made of an aluminum alloy, is generally referred to as a valve body. The components of the system are assembled in the valve body. Certain features of the valve body may be machined after casting, such as grooves and face surfaces. The speed and/or quality of the machining operations may be affected by vibrations, such as from the system or harmonics.

SUMMARY

In at least one embodiment, a method is provided. The method may include moving a milling tool having at least two axially spaced apart sets of cutting inserts to an axial position within a bore in a material; rotating the milling tool about a longitudinal axis; initiating contact between the milling tool and a wall of the bore in a region of the wall having a least amount of material at the axial position; and moving the milling tool around a perimeter of the bore.

The moving step may include moving the milling tool around an entire perimeter of the bore at the axial position at least once to form at least one groove in the bore. In one embodiment, the moving step includes moving the milling tool around an entire perimeter of the bore at the axial position at least once to form a face and a groove in the bore. The initiating step may include moving the milling tool in an arcuate path and contacting the wall of the bore at an acute angle. In one embodiment, the wall may at least partially define at least two channels extending perpendicular to and intersecting the bore, and each of the at least two axially spaced apart sets of cutting inserts is aligned with one of the at least two channels when the milling tool is in the axial position such that moving the milling tool around the perimeter of the bore enlarges the at least two channels aligned with the sets of cutting inserts. The at least two channels aligned with the sets of cutting inserts may each be tapered such that they are wider at a first end than at a second end; and the initiating step may include initiating contact between the milling tool and the wall of the bore in a region of the wall including the first ends of the at least two channels.

In one embodiment, the method may include supplying lubricant in a pneumatic stream through the milling tool to at least one of the sets of cutting inserts while moving the milling tool around the perimeter of the bore. A flowrate of the lubricant supplied in the pneumatic stream may be from 5 to 200 ml/hour. Prior to the moving step, the method may further include performing modal testing on at least one of the milling tool or the material; and generating a depth of cut vs. spindle speed stability lobe diagram including a plurality of adjacent lobes based on the modal testing; wherein a depth of cut and a spindle speed of the milling tool during the moving step are set to a point between a pair of adjacent lobes in the stability lobe diagram.

In at least one embodiment, a method is provided. The method may include moving a milling tool including two axially spaced apart sets of cutting inserts to an axial position within a bore; rotating the milling tool about a longitudinal axis; initiating contact between the milling tool and a wall of the bore in a region of the wall having a least amount of surface area at the axial position; and moving the milling tool around a perimeter of the bore.

In at least one embodiment, an interpolated milling tool is provided. The tool may include a tool shaft having a longitudinal axis; a first set of radially spaced cutting inserts coupled to the tool shaft; and a directly adjacent second set of radially spaced cutting inserts coupled to the tool shaft and spaced from the first set of cutting inserts along the longitudinal axis. The first and second sets of cutting inserts may be staggered from each other by at least 10 degrees. The tool shaft may include an axial lubricant passage and at least one radial lubricant passage may communicate with the axial lubricant passage and be configured to deliver lubricant to each set of cutting inserts.

The first and second sets of cutting inserts may be staggered from each other by at least 40 degrees. In one embodiment, the first and second sets of cutting inserts each include three cutting inserts and the first and second sets of cutting inserts are staggered from each other by about 60 degrees. The tool may include a third set of set of radially spaced cutting inserts coupled to the tool shaft directly adjacent to the second set of inserts, opposite the first set of inserts, and may be spaced from the second set of inserts along the longitudinal axis. The first, second, and third sets of cutting inserts may be staggered from each other by at least 20 degrees. In one embodiment, the first, second, and third sets of cutting inserts are staggered from each other by about 40 degrees. The first set of cutting inserts may have a larger cutting radius than the second set of cutting inserts. In one embodiment, the first and second set of cutting inserts each have a positive rake angle.

BRIEF DESCRIPTION OF THE DRAWINGS

FIG. 11 is a diagram of a milling tool path, according to an embodiment;

FIG. 12 is a table of coordinates associated with the points in FIG. 11;

FIG. 13 is an example of a stability lobe diagram for a milling tool; and

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Commonly owned U.S. Pat. No. 8,555,503, filed Jul. 20, 2011 describes tools and methods for interpolated milling and the disclosure of which is hereby incorporated in its entirety by reference herein. The tools and methods in the present disclosure may be applied to the tools and methods disclosed in the above patent, and vice versa. The above patent also discloses tools and methods that include supplying lubricant in a pneumatic stream through the tool to the cutting edges. The amount of lubricant used may be very small, which may be referred to as minimum quantity lubricant (MQL). For example, the flow rate of the lubricant may be from 10 to 200 ml/hour. In view of the present disclosure, one of ordinary skill in the art will be able to combine embodiments or elements of the two disclosures.

Figure 1:
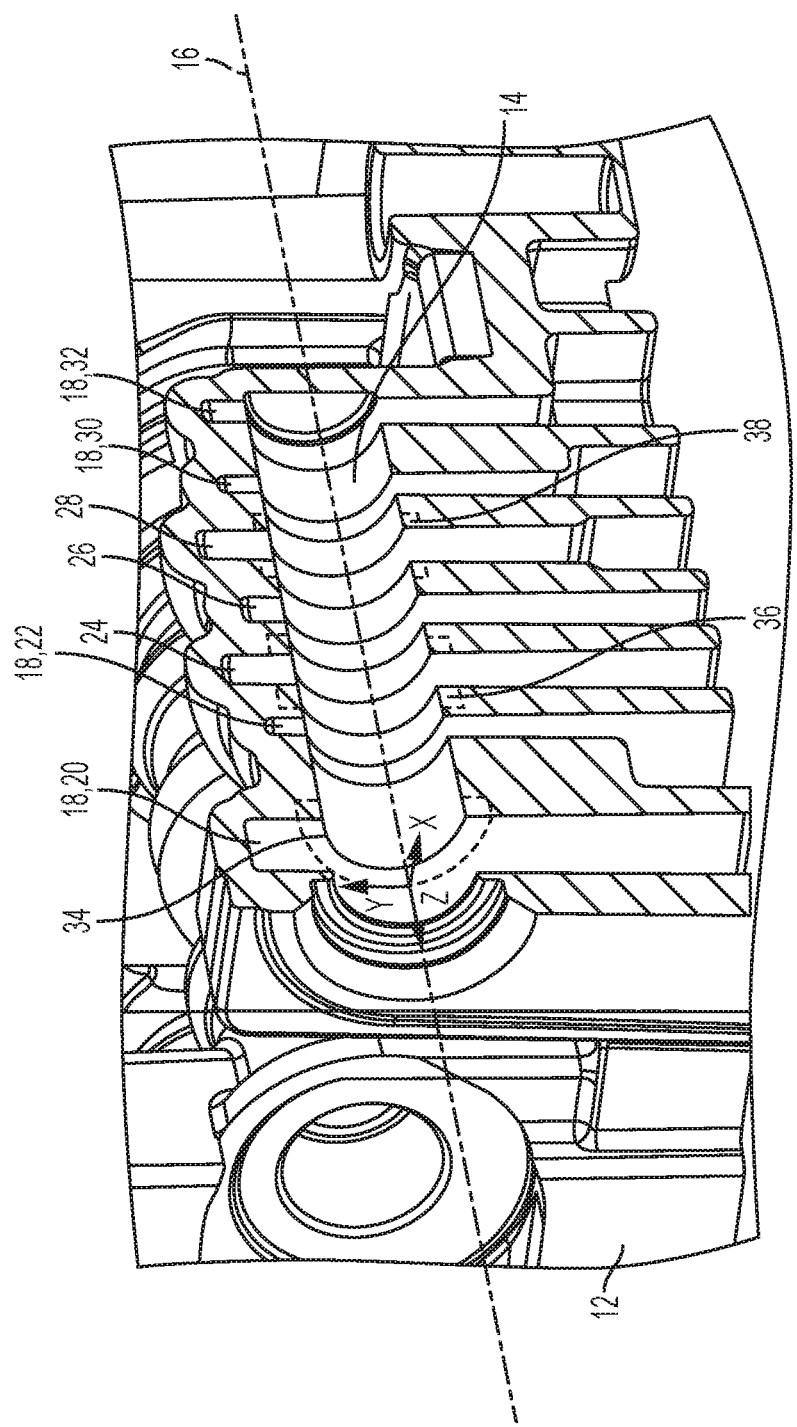
FIG. 1 is a perspective view of a cross-section of a valve body, according to an embodiment.
Figure 2:
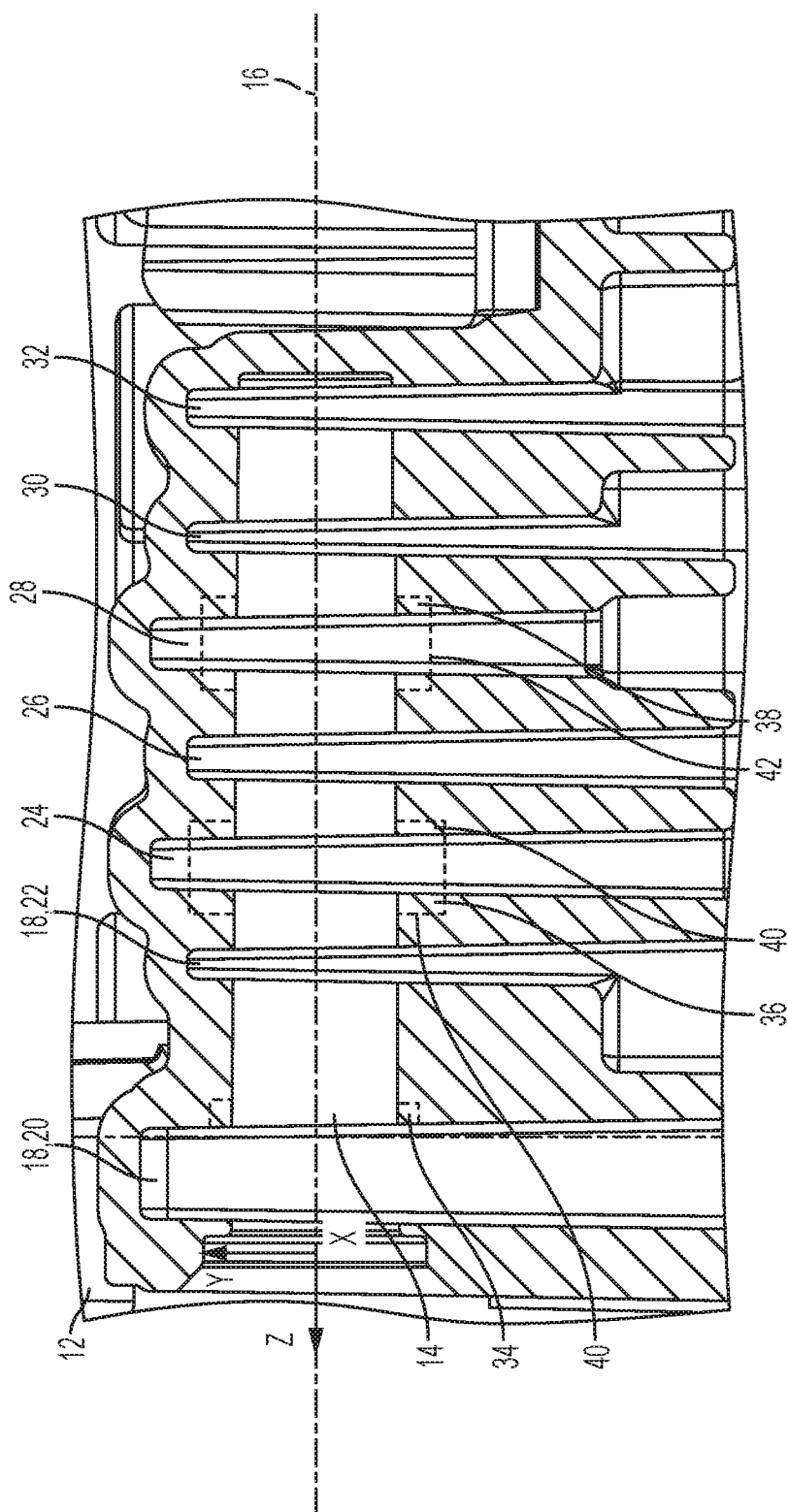
FIG. 2 is a side view of the cross-section of FIG. 1.

With reference to FIGS. 1-2, a valve body 12 is shown. The valve body 12 may contains a valve, such as a casting-integrated, direct acting solenoid hydraulic valve, for example, as described in U.S. Pat. No. 8,555,503. However, the disclosed valve body 12 may be used in other valves. In addition, the present disclosure may be implemented in areas other than valve bodies, and may be used in any situation in which multiple grooves, edges, and/or faces are machined at once. The valve body 12 may be a casting, such as a metal casting. In one embodiment, the valve body 12 may be cast aluminum (e.g., pure or an alloy thereof). Any suitable casting method may be used, such as die-casting (e.g., high pressure die-casting).

The valve body 12 may include a bore 14 therein, which may have a central axis 16. The bore 14 may be cylindrical or substantially cylindrical. The bore 14 may be cast-in to the body 12 or may be machined thereafter. In at least one embodiment, the valve body 12 may include channels or passages 18 formed therein, which may be perpendicular to the central axis 16. In the embodiments shown in FIGS. 1 and 2, there are seven channels 18, which may be labeled 20, 22, 24, 26, 28, 30, and 32 (from left to right). The channels 18 may be formed during casting, for example, using inserts in the mold. The inserts may be tapered, also referred to as having a draft angle, in order to facilitate removal from the casting. As a result, the channels 18 may have a taper or draft angle. In the embodiments shown, the channels taper such that they are narrower at the top and wider at the bottom. However, the taper may be from any angle, depending on how the inserts are positioned.

After casting the valve body 12, one or more machining operations may be performed to add grooves, edges, or faces in the valve body 12. In at least one embodiment, the grooves, edges, or faces may be formed in one or more of the channels 18. For example, in the embodiments shown, channels 20, 24, and 28 may have a groove or face formed therein. A face 34 is shown extending from one side of channel 20 and grooves 36 and 38 are shown expanding channels 24 and 28 on both sides. Since the channels 18 have a taper or draft angle, more material may be removed from the top of the face 34 and grooves 36 and 38 than the bottom. The faces and/or grooves may be formed with two side walls 40 that are perpendicular to the central axis 16 and one end wall 42 that is parallel to the central axis 16. However, in other embodiments, one or both of the sides walls 40 may be tapered or have a chamfer.

While the embodiments of the valve body 12 shown include one face and two grooves formed therein, there may be more or less faces and/or grooves in any combination. There may be one or more grooves and/or faces. In one embodiment, a total number of faces and grooves may be at least two, such as at least 3 or 4. In another embodiment, the total number of faces and grooves may be from 2 to 5, such as 2 to 4 or 2 to 3. At least two of the total number of faces and grooves may be formed in a single machining operation. For example, a single machining operation (e.g., interpolated milling) may form at least 3 or at least 4 faces/grooves. In one embodiment, all of the total number of faces and grooves may be formed in a single machining operation.

The faces and/or grooves may be formed by an interpolated milling process. Interpolated milling may include inserting a milling tool into a bore (or other opening), the milling tool having a smaller diameter/radius than the bore. The milling tool may rotate around its own longitudinal axis and also be moved in a path around the perimeter or circumference of the bore to remove material therefrom. In the case of a bore having a circular cross-section, the milling tool may be rotated around a circular cutting path that results in a larger groove radius than the radius of the bore (the cutting path and the bore may share a common center). Accordingly, the amount of material removed from the bore wall may be the cutting radius (e.g., from cutting edge to bore center) minus the bore radius. The milling tool may make one or more revolutions or passes around the circumference of the bore. The cutting radius may be increased during subsequent passes or may be kept the same to ensure a more cylindrical surface after the milling process.

In at least one embodiment, there may be a facing operation included in the formation of the faces and/or grooves. Facing may include cutting in a direction perpendicular to the longitudinal axis of the tool. However, the same tool may be used to perform the facing operation and the interpolated milling operation. In one example, a first or most proximal set of inserts may perform the facing operation, while the remaining sets of more distal inserts perform only interpolated milling operations. In this example, the first set of inserts may have a diameter that is larger than a portion of the bore, therefore, when inserting the tool axially into the bore the first set of inserts may make contact with the portion of the bore. The rotation of the tool may make a face cut into the portion of the bore, thereby increasing its diameter to the diameter of the tool cutting inserts. After the facing operation, the tool may be interpolated and the first set of inserts may further increase the diameter of the bore from the faced diameter to a larger diameter, as described above.

Figure 3:
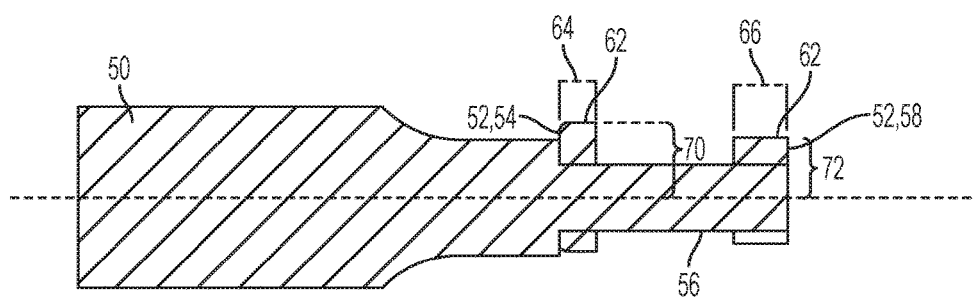
FIG. 3 is a cross-section of a milling tool, according to an embodiment.
Figure 4:
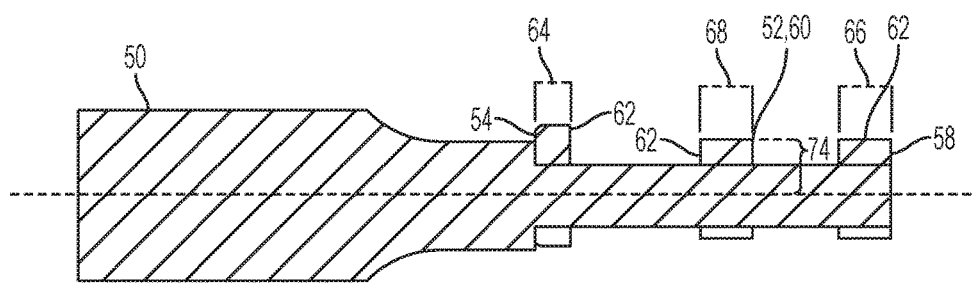
FIG. 4 is a cross-section of another milling tool, according to an embodiment.

The interpolated milling process may be performed using a milling tool 50, examples of which are shown in FIGS. 3 and 4. The same tool 50 may also perform the facing operation, in embodiments where one is included. The embodiment of the tool 50 shown in FIG. 3 includes two sets of cutting inserts 52, while the embodiment shown in FIG. 4 includes three sets of cutting inserts 52. A first set 54 of inserts 52 may be disposed at or near a proximal end of the tool shaft 56, while a second set 58 of inserts 52 may be disposed at or near a distal end of the tool shaft 56. The axial distance between first set 54 of inserts 52 and second set 58 of inserts 52 along the axial direction of the milling tool is greater than the cutting depth of the first set 54 of inserts 52 and second set 58 of inserts 52. The shaft of tool 50 has an outer surface and a radius. A distance between the cutting edge of each of the inserts 52 of the first set 54 and the tool shaft outer surface is greater than the tool shaft radius. In the embodiment shown in FIG. 4, a third set 60 of inserts 52 may be disposed between the first and second sets. There may be additional sets of inserts 52, which may be disposed between the first, second, and third sets.

Each set of cutting inserts may have one or more cutting inserts 52. For example, each set may include 2, 3, 4, 5, or more inserts. Each set of inserts may have the same number of inserts, however, it is not required. Each insert 52 in a set of inserts may be at the same or substantially same longitudinal position on the tool shaft 56. Each insert 52 may also have the same size cutting surface, same rake angle, and/or other attributes. The number of sets of inserts 52 may correspond to the number of faces and grooves that are to be formed in the valve body 12. For example, if there are two grooves and one face to be machined into the valve body 12, there may be three sets of cutting inserts, such as shown in FIG. 4.

Accordingly, the positioning of the sets of cutting inserts may also correspond to the locations of the grooves/faces to be machined into the valve body 12. The cutting inserts 52 of each set may have a cutting edge 62 having a cutting length (e.g., parallel to the tool shaft and center axis 16). The first, second, and third sets of inserts may have cutting lengths 64, 66, and 68, respectively. The cutting length of the inserts may determine the length of the groove/face that is machined into the valve body. For example, if the tool of FIG. 4 was used to machine face 34 and grooves 36 and 38 in FIGS. 1 and 2, then the length of face 34 and grooves 36 and 38 may be determined by the cutting lengths 64, 68, and 66, respectively (third set is between first and second sets).

In addition to having cutting lengths, each set of cutting inserts may have a cutting radius or cutting depth (e.g., distance perpendicular to the tool shaft and center axis). Similar to the cutting length, the cutting radius may determine the depth of the faces and/or grooves formed by the tool. In the example shown in FIGS. 3 and 4, the first set 54 of inserts has a cutting radius 70 that is larger than a cutting radius 72 of the second set 58 of inserts. In the example shown in FIG. 4, the third set 60 of inserts has a cutting radius 74 that is the same as the cutting radius 72. However, these are merely examples, and each set of inserts may have a different cutting radius, the same cutting radius, or any mix of cutting radii. Similarly, the first set 54 of inserts does not necessarily have the largest cutting radius nor the second/third sets 58, 60 the smallest.

Figure 5:
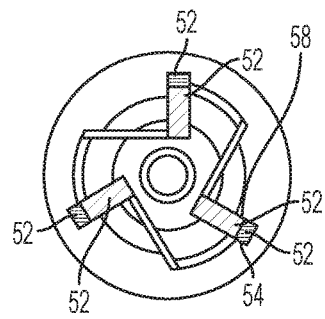
FIG. 5 is an end view of a milling tool having aligned cutting inserts, according to an embodiment.
Figure 6:
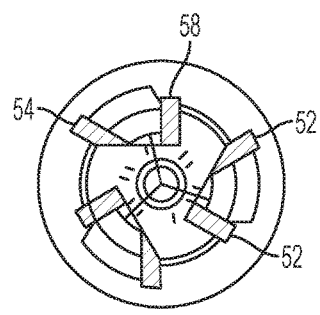
FIG. 6 is an end view of a milling tool having staggered cutting inserts, according to an embodiment.
Figure 7:
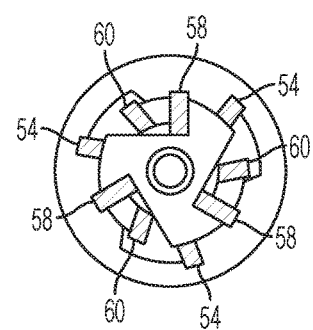
FIG. 7 is an end view of another milling tool having staggered cutting inserts, according to an embodiment.

With reference to FIGS. 5-7, several examples of insert arrangements are shown in end view. In each of FIGS. 5-7, each set of inserts includes three spaced apart inserts 52. In FIG. 5, each set of inserts is aligned with the others. As shown in FIG. 5, the inserts are equally spaced with one insert in each set located at 0°, another at 120°, and another at 240°. Accordingly, in end view, the sets are only distinguishable because of their different cutting radii. Similar to FIG. 3, the first set 54 of inserts 52 has a cutting radius 70 that is larger than the cutting radius 72 of the second set 58. Therefore, the inserts 52 of the first set 54 extend radially outward passed the inserts of the second set 58

In the embodiments shown in FIGS. 6 and 7, the sets of inserts are staggered relative to one another. In the example shown in FIG. 6, the first set 54 and the second set 58 are staggered 60 degrees from each other. Similar to FIG. 3, the first set 54 of inserts 52 has a cutting radius 70 that is larger than the cutting radius 72 of the second set 58. As shown in FIG. 6, the second set 58 of inserts are equally spaced with one insert located at 0°, another at 120°, and another at 240°. Accordingly, the second set 58 inserts are located in the same positions as in FIG. 5. However, the first set 54 of inserts are equally spaced with one insert located at 60°, another at 180°, and another at 300°.

In the example shown in FIG. 7, there are three sets of inserts, similar to FIG. 4. In this embodiment, the first set 54, the second set 58, and the third set 60 are staggered 40 degrees from each other. As shown in FIG. 7, the third set 60 of inserts are equally spaced with one insert located at 0°, another at 120°, and another at 240°. The first set 54 of inserts are equally spaced with one insert located at 40°, another at 160°, and another at 280°. The second set 58 of inserts are equally spaced with one insert located at 80°, another at 200°, and another at 320°.

While FIGS. 6 and 7 show two examples of staggered inserts, 60 and 40 degrees, other staggering angles may also be used. For example, the inserts may be staggered by 10 to 80 degrees, or any sub-range therein, such as 20 to 70 degrees, 30 to 70 degrees, 30 to 60 degrees, or 40 to 60 degrees. In one embodiment, the inserts may be staggered by at least 15, 20, 25, or 30 degrees. In at least one embodiment, the staggering values disclosed above are between adjacent sets of inserts. In another embodiment, there may be the disclosed staggering between all sets of inserts on the tool. The staggering may depend on the number of sets of inserts or the number of inserts in each set. The sets are shown with three inserts, however, other numbers may be used. For example, if there were four inserts per set, they may be spaced at 90 degrees and the sets may be staggered at 45 degrees.

In addition to staggering the sets of inserts, each set of inserts may be equally spaced or unequally spaced. For example, if there are three inserts then equal spacing would be 120 degrees between each insert and if there are four inserts then equal spacing would be 90 degrees. However, the inserts within each set may also be unequally spaced. For example, if there are three inserts then they may have spacings of 117, 121, and 122 degrees. Similarly, for four inserts, an example of unequal spacings may be 87, 89, 91, and 93 degrees. These values are merely examples, however, and are not intended to be limiting. In one embodiment, the sets of inserts may include at least two unequally spaced inserts. In another embodiment, the sets of inserts may include all unequally spaced inserts (e.g., no two inserts equally spaced). The inserts may be unequally spaced by up to 2, 3, 5, or 10 degrees.

It has been discovered that staggering the sets of inserts and/or unequally spacing the inserts may assist in reducing vibration in the system during the milling operation. For example, unequal spacing of the inserts within each set of inserts may break-up the harmonic excitation by the cutter. Staggering the sets of inserts may also reduce vibration, but it is believed to do so by reducing the exciting force. For example, when using the milling tool of FIG. 6, instead of two sets of milling tools impacting the work material at once (e.g., like FIG. 5), there will be two separate impacts for every insert in the set. Similarly, the tool of FIG. 7 would have three separate impacts for every insert in the set. Accordingly, the force applied by the tool, which may be an exciting vibrational force, is reduced and spread out over multiple impacts. The two approaches may be used separately or together. Therefore, staggered and unequally spaced sets of inserts may reduce both the exciting force and break-up the harmonic excitation of the cutter.

Figure 8:
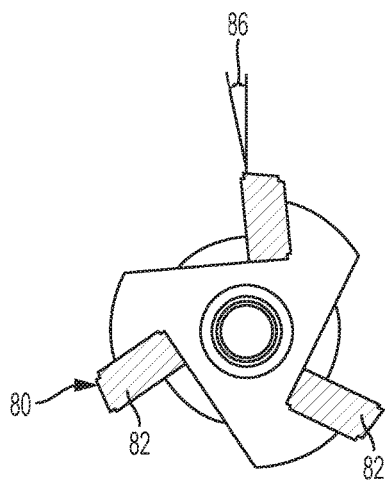
FIG. 8 is an end view of a milling tool having cutting inserts with a positive rake angle, according to an embodiment.
Figure 9:
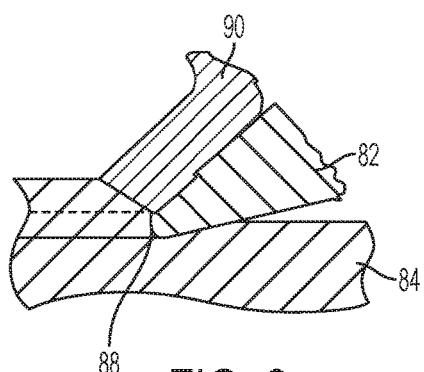
FIG. 9 is a schematic cross-section of a cutting inserts removing a chip of material from a workpiece, according to an embodiment.

With reference to FIGS. 8 and 9, an end view of a single set 80 of inserts 82 and a schematic cross-section of an insert 82 cutting the work material 84 are shown. In addition to staggering and/or unequally spacing the inserts, it has been found that the rake angle 86 of the inserts may also affect the vibration in the system. The rake angle 86 may describe the angle of the cutting surface relative to the work material. A positive rake angle, shown in FIGS. 8 and 9, is formed when the cutting surface angles into the work piece. A negative rake angle is formed when the cutting surface angles away from the work piece and a zero or neutral rake angle is formed when the cutting surface is perpendicular to the work piece. In particular, it has been found that a positive rake angle may reduce the cutting force. In one embodiment, the cutting inserts on one or more of the sets of inserts may have a rake angle of −20 to +30 degrees. In another embodiment, the rake angle may be from −5 to +10 degrees. In another embodiment, the rake angle may be from 0 to +30 degrees. In another embodiment the rake angle may be from +5 to +30 degrees.

With reference to FIG. 9, in addition to the rake angle 86, the cutting edge 88 of the insert 82 may also affect the cutting operation. As shown in FIG. 9, the insert 82 removes material from the work material 84 one chip 90 at a time. The cutting edge 88 may have varying degrees of sharpness, which may be referred to as edge preparation. The degree of edge preparation may affect the cutting force required and the durability of the insert, among other things. A low degree of edge preparation may refer to a less rounded or more sharp cutting edge 88, while a high degree of edge preparation may refer to a more rounded or less sharp cutting edge 88. In one embodiment, the cutting edge 88 may have a radius of 0.005 to 0.05 mm. A cutting edge with a high degree of edge preparation may be more durable and/or have a longer tool life than a cutting edge with low edge preparation. The degree of edge preparation may also depend on the material of the cutting edge 88. In one embodiment, the cutting insert and/or edge may be formed of a polycrystalline diamond (PCD), cubic boron nitride (CBN), carbide, silicon nitride ($Si_3N_4$), or any other cutting insert material. These inserts materials may be coated, but a coating is not necessary.

Figure 10:
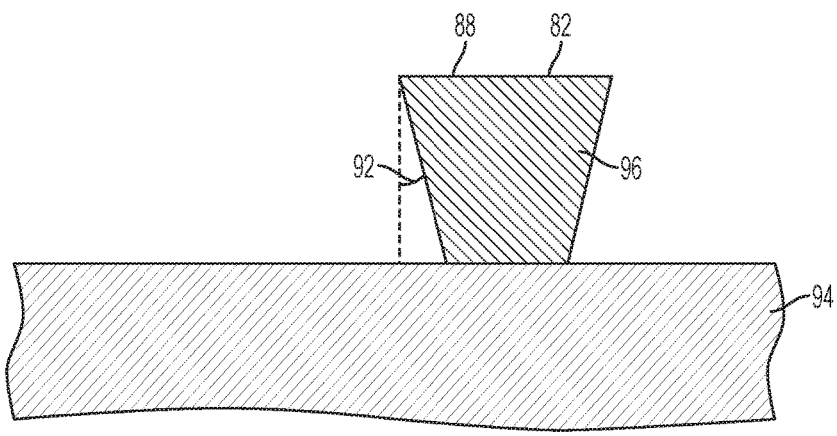
FIG. 10 is a schematic cross-section of a cutting insert having a lead angle, according to an embodiment.

With reference to FIG. 10, in addition to rake angle and edge preparation, the inserts 82 may also include a relief or clearance angle 92. The relief angle may be a taper of the cutting insert 82 from the cutting edge 88 towards the tool body 94. The relief angle may prevent the sides 96 of the cutting insert from contacting the newly formed surfaces of the work material as the cutting edge 88 extends into the work material. This may ensure a smoother and/or more precise groove or face is formed. In one embodiment, the relief angle may be from 1 to 15 degrees.

Any or all of the features described with respect to FIGS. 3-10 may be incorporated into a milling tool in any combination. The milling tool may be used to create grooves, faces, and/or edges, such as those shown and described with respect to FIGS. 1 and 2. The features may also be incorporated into the tools shown and described in U.S. Pat. No. 8,555,503, and vice versa. For example, the lubricant passages (e.g., axial and radial) and their operation disclosed in U.S. Pat. No. 8,555,503 may be incorporated into the disclosed tools and methods. In addition to the disclosed tools and cutting insert features, methods of machining are also disclosed. The methods may be carried out using the disclosed and incorporated tools and cutting insert features, however, they may also be carried out using known or conventional tools or tools developed in the future.

The disclosed tools may be used to form internal faces and grooves in a bore, which may be smooth faces/grooves. The tools may be used in a finishing machining operation (e.g., after a rough or semi-finish operation). The cutting inserts may each have the same cutting edge shape. The sets of cutting inserts may have an even or odd number of cutting inserts per set. The cutting inserts may be replaceable. As described above, the spacing between the inserts within each set of inserts may be uniform or it may be irregular. In addition, the rake angle of the inserts within each set of inserts may be uniform or irregular. The tool may be configured such that it cuts at distinct axial locations along the bore. For example, there may be two or more spaced apart sets of inserts that form two or more spaced apart faces/grooves in the bore (e.g., not continuous axial cutting).

With reference to FIG. 11, a schematic diagram 100 is shown that represents a tool path 102 during an interpolated milling operation. The tool path 102 is an example of a tool path that may be used for the valve body 12 shown in FIGS. 1 and 2. FIG. 12 shows an example of a position chart for the points shown in FIG. 11. The X, Y, and Z positions correspond to the X, Y, and Z axes shown in FIGS. 1 and 2, with the X axis coming out of the page, the Y axis in the vertical direction, and the Z axis corresponding to the center axis 16, respectively, in FIG. 2. Accordingly, a point at 0, 0 in the X-Y plane corresponds to a point on the center axis 16. The Z axis is not shown in FIG. 11, since the path takes place in two dimensions. However, the Z axis is coming into/out of the page, similar to the X axis in FIG. 2.

In conventional interpolated milling operations, the point of first contact between the tool and the work material is random and the main requirement is that at least one full revolution is made. However, it has been discovered that the initial point of contact may have a significant impact on the milling operation. The impact not only affects the initial cut, but may affect the entire milling operation. It has been found that an initial contact with the work material at a region with the least material to be removed, also called the least material condition (LMC), may significantly reduce the cutting force of the milling operation. The cutting force may not only be reduced for the initial cut, but for the entire cutting operation (e.g., one or more full revolutions). Lower forces may result in reduced vibration amplitude.

As described above, a face 34 and two grooves 36, 38 are to be formed in channels 20, 24, and 28 of the valve body 12 shown in FIGS. 1 and 2. The channels may have a draft angle in order to facilitate removal from the casting. As a result, the channels may be narrower at the top and wider at the bottom. Accordingly, there is less material to be removed from the bottom of the valve body 12 at the bottom of the bore 14 than at the top. Therefore, in at least one embodiment, the interpolated milling process may be programmed to make initial contact with the bore wall at or near the bottom of the bore wall where there is the least material to be removed. This area or region may also correspond to a region where there is the least amount of surface area of the bore wall. The tool may engage the work material at a point or region where the least material is to be removed (or where there is the least surface area) and be fully engaged with the work material before it reaches the region with the greatest material to be removed.

In the example shown in FIGS. 11 and 12, the milling tool may start at a center location, identified as point 1. The points may correspond to a center longitudinal axis of the milling tool. Point 1 may place the tool at or near the center axis of the bore 14 and at a predetermined axial location in the bore 14. In this example, point 1 corresponds to point 0, 0, −42.5 in the XYZ coordinate system. As shown in FIG. 12, the Z location of the tool may stay constant during the entire milling process (e.g., no axial movement within the bore). Accordingly, the faces/grooves/edges may be cut at the same time. Alternatively, each face/groove could be cut one at a time by moving the tool in the Z axis and performing another interpolated milling process.

To begin the interpolated milling process, the tool may be moved to point 2, corresponding to 1.125, −1.125 in the XY coordinate system. There may, of course, be points located between the identified point numbers, however, not all point are specifically identified. One of ordinary skill in the art will understand, based on the present disclosure, the intermediate points may be programmed. The movement from point 1 to point 2 may be an arcuate path, as shown, however it is not required (e.g., could be a straight line). From point 2, the tool may be moved to point 3 at 0, −2.25 in the XY system. The tool may make contact with the bore wall at, or just prior to reaching, point 3. As described above, point 3 may correspond to a region having the least material to be removed by the interpolated milling process and/or where there is the least surface area of the bore wall at that axial location. Similar to the movement from point 1 to point 2, the movement from point 2 to point 3 may be an arcuate path. This may allow the cutting inserts to first contact the bore wall at an angle, rather than perpendicularly.

From point 3, the milling tool may follow a circular path around the perimeter or circumference of the bore wall to removed material therefrom. The circular path may have a cutting radius from the center of the bore that is a certain amount greater than the original bore radius, thereby forming a face, groove, or edge extending from the bore by the predetermined amount. The tool may be moved to point 4, corresponding to −2.25, 0 on the XY system, or the left side of the bore as shown in FIG. 1. The tool may continue to point 5, corresponding to 0, 2.25 on the XY system, or the top of the bore as shown in FIG. 1. Point 5 may correspond to a region of the bore where the most material is to be removed, due to the taper of the channels. As described above, it has been discovered that by starting the milling process in the area of least material, the cutting forces may be reduced for the entire cutting path, including the area of greatest material to be removed. By the time the tool has reached point 5, it has fully engaged with the bore wall and therefore less force is required to make the cut.

From point 5, the tool may continue to point 6, corresponding to 2.25, 0 on the XY system, or the right side of the bore as shown in FIG. 1. From point 6, the tool may continue in the circular path back to point 3, the initial contact point of the tool and the bottom of the bore at 0, −2.25. Points 1-6 therefore describe an initial revolution of the tool around the bore wall to form faces and/or grooves. The tool may be programmed to perform additional revolutions around the bore wall, or the process may be completed after a single revolution. If additional revolutions are performed, they may be at the same depth or the depth may be increased to further increase the depth of the faces/grooves. If the revolutions are at the same depth, the path may be the same or substantially the same as the path from points 3 to 6 and back to 3, described above. If the revolutions are at a different depth, then the path shape may be similar to above, but with larger X and Y values (e.g., absolute values). However, the additional revolutions may still be performed at the same Z value, such that the tool does not move in the axial direction.

As described above, the path 102 shown and described in FIGS. 11 and 12 is merely an example, and is not intended to be limiting. The region of least material may be located anywhere within the bore wall (or other passage, not necessarily cylindrical). Accordingly, the point 3 (point of first contact) may be at any location where there is the least material to be removed. It has been found that the disclosed interpolated milling cutting path may reduce the cutting force of the milling operation by about 33%. For example, a cut beginning at point 5 instead of point 3 may require a 200 Newtons peak force, instead of a 150 Newtons peak force at point 3. By reducing the cutting force, the vibration exciting force is also reduced, which may improve the cutting process tool life and part quality.

In addition to, or instead of, changes to the tools, inserts, and/or milling path, it has been found that improvements to the interpolated milling process may result from analyzing the vibration properties of the components in the system and identifying regions of high performance. There may be two different type of vibrations considered in the analysis, forced vibrations from the interaction of the milling tool and the work material and harmonic vibrations that occur due to the harmonic frequencies of the components By tuning of the tool, the self-excited vibrations may be minimized. The design of the tool disclosed above may reduce forced vibrations.

In at least one embodiment, modal testing may be performed on the components of the milling system, such as the tool (with or without inserts) and the work material (e.g., valve body). Modal testing is a type of vibration testing wherein the natural frequencies, modal masses, modal damping ratios and mode shapes of tested object are determined. Modal testing may be performed using several methods, which may include impact hammer modal testing or shaker modal testing. In both methods, energy with a known frequency is applied to the system and the response spectra is analyzed. A transfer function, or frequency response function, may be determined using the response spectra and a force spectra. Impact hammer testing includes striking the component very quickly with a hammer.

Once the modal parameters of the components in the system have been determined, stability analysis may be used to convert the tool-point frequency response functions to a stability lobe diagram, an example of which is shown in FIG. 13. The stability lobe diagrams may include a Y-axis of depth of cut and a X-axis of spindle speed (e.g., rotation speed—rpm). The lobes that are shown describe areas of predicted instability—areas within the lobe are unstable and areas below the lobe are stable. There are several sets of lobes shown in FIG. 13, which may represent different models. For example, the diagonal dashed region represents an unstable region and the horizontal hatched region represents 20 percent uncertainty around the stability boundary. The vertical bands shown in the diagram correspond to harmonic of the system natural frequencies. These regions may be avoided. Areas between adjacent lobes may represent potentially beneficial regions of operation where the depth of cut can be relatively large but still stable. In addition, areas between adjacent lobes and between the vertical harmonic bands may be even more stable. In particular, areas between adjacent lobes at the right side of the diagram may represent areas of large depth of cut and high spindle speed, which may allow for relatively fast and deep material removal, while remaining stable.

Previously, the spindle speed and/or depth of cut was determined by trial and error or the depth of cut was kept relatively small since, as shown in FIG. 13, all spindle speeds are stable under a certain threshold of depth of cut (e.g., about 0.085 inches, in FIG. 13). However, by performing modal testing on the components of the system and modeling the vibration performance, deeper and faster cutting operations may be performed with a greater expectation of stability. The optimal regions between the lobes may vary based on the tool configuration (e.g., insert configuration), the tool material, the material being machined, or other factors. Accordingly, to identify optimal regions, a new stability lobe analysis may have to be performed if one or more of these factors are changed between machining operations.

Figure 14:
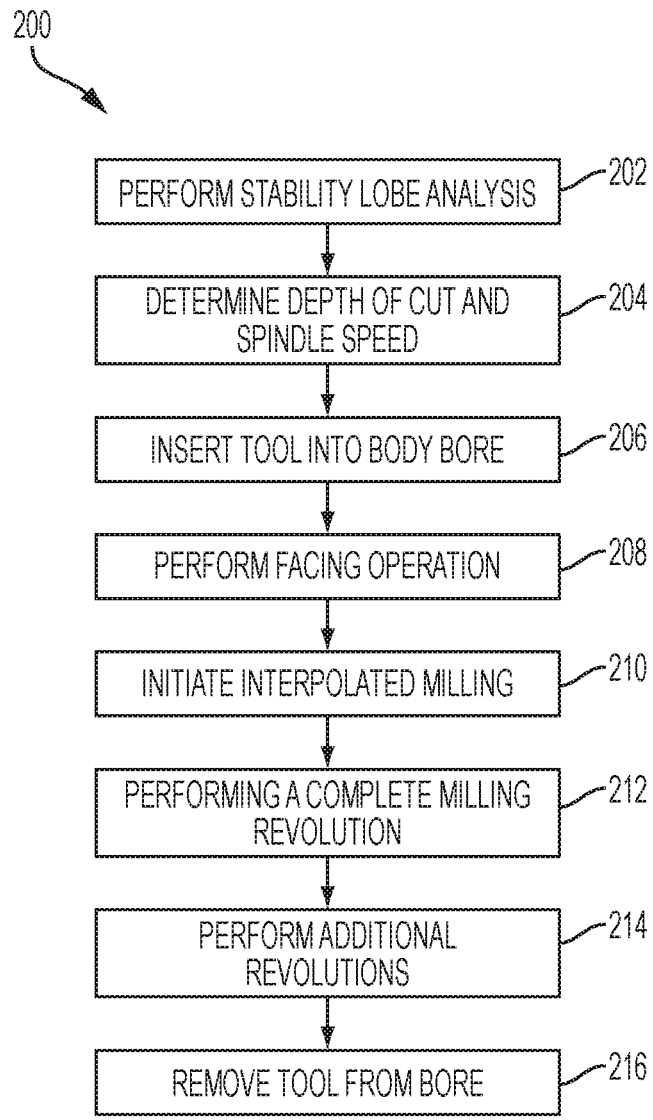
FIG. 14 is a flowchart for a method of milling one or more grooves in a valve body, according to an embodiment.

With reference to FIG. 14, an example of a flowchart 200 is shown of a method of machining a valve body. However, the method may also apply to machining processes other than valve bodies. One of ordinary skill in the art will appreciate that steps may be added to or removed from the flowchart 200, or that steps may be rearranged.

In step 202, a stability lobe analysis may be performed prior to the machining process. The generation of the stability lobe diagram is described above and will not be repeated in detail. Some or all of the components of the system, including the milling tool and the body to be machined may be testing using modal analysis (e.g., impact hammer test). Then, the modal parameters from the testing may be input into a computer model to generate a stability lobe diagram. In step 204, a depth of cut and/or spindle speed may be determined based on the stability lobe diagram. As described above, gaps or spaces between adjacent lobes may provide regions of higher system performance, for example, allowing greater depths of cut and/or spindle speed without instability. This step may be repeated if one element of the system (e.g., part, tool, tool holder, machine, fixture, machining parameters, etc) changes.

In step 206, a milling tool may be inserted into the bore of the valve body (or bore of another object). The milling tool may have a longitudinal axis or axis of rotation, and the insertion may be in the axial direction. The tool may be inserted along a center axis of the bore (e.g., a 0, 0 XY coordinate). During the insertion, the milling tool may be rotating about the longitudinal axis or it may be static. As part of the insertion, an optional facing operation may be performed in step 208. As described above, a first or proximal set of inserts may perform the facing operation. The bore may include a portion having a diameter than is less than that of the first set of inserts but larger than the remaining sets of more distal inserts. The portion may include a shoulder relative to a more proximal portion of the bore (e.g., perpendicular portion, or nearly perpendicular). Accordingly, the more distal inserts may extend into the bore passed the bore portion without contacting the bore portion. The first set of inserts may contact the bore portion having a smaller diameter while rotating and may machine a face into the bore. The inserts may contact the shoulder portion. The face may have a length that is the same or substantially the same as a length of the cutting inserts. The face may have one wall that is substantially perpendicular to the longitudinal axis and one wall that is substantially parallel thereto.

In step 210, an interpolated milling process may be initiated. As described above, the tool may make first contact with the work material in regions where the least material is to be removed. For example, if grooves are to be formed in cast-in channels, the channels may have a draft to them such that the channels are tapered. In this example, the first contact between the sets of cutting inserts and the channels may be at the wider end of the channel. Accordingly, the widest part of the channel will have less material to be removed. It has been discovered that starting or initiating the interpolated milling process at this point may significantly reduce the amount of cutting force necessary for the machining process.

In step 212, once the milling process is initiated in step 210, a complete revolution of the milling tool around the circumference or perimeter of the bore may be performed. The revolution may be performed while maintaining the axial position of the tool constant (e.g., the tool does not move axially within the bore, no change in Z position). The revolution may remove a predetermined depth from the bore to create or expand a face and/or groove. There may be two or more sets of axially spaced cutting inserts, therefore, multiple faces or grooves may be formed or expanded during a single revolution of the tool around the bore. The sets of inserts may have the same or different cutting radii, therefore, the depth of the faces or grooves may be the same or different. One revolution around the bore may be sufficient to form the faces and/or grooves. The interpolated milling revolution may be performed according to the stability lobe analysis in step 202. The depth of cut and/or the spindle/rotation speed may be selected such that it is in an area between two adjacent stability lobes in the diagram. Alternatively, each side of the groove could be cut independently.

In step 214, the method may optionally include performing additional revolutions of the tool around the bore. The additional revolutions may be performed around the same path to ensure a precise or more uniform face/groove depth or the additional revolutions may remove additional material from the bore to enlarge the faces/grooves. The number of additional revolutions may depend on the amount of material to be removed. The number of revolutions may therefore also at least partially depend on the stability lobe analysis in step 202. For example, if the depth of cut is able to be increased within certain windows in the stability diagram, then the number of revolutions may be reduced. In one embodiment, there may be from 1 to 5 additional revolutions, or any sub-range therein, such as 1 to 4, 1 to 3, 2 to 3, or 1 to 2.

In step 216, the tool may be removed from the bore. This may be performed by re-centering the tool in the bore, for example, to a 0, 0 XY location or to the same coordinates as the initial insertion. However, any coordinates that will avoid the inserts of the tool from contact the bore wall may be used.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An interpolated milling tool, comprising:
    a tool shaft having a longitudinal axis;
    a first set of radially spaced cutting inserts coupled to the tool shaft and disposed along a first longitudinal region of the longitudinal axis; and a directly adjacent second set of radially spaced cutting inserts coupled to the tool shaft, disposed along a second longitudinal region of the longitudinal axis, and spaced from the first set of cutting inserts along the longitudinal axis an axial distance, the first and second regions non-overlapping along the longitudinal axis;

the first and second sets of cutting inserts each having a cutting edge parallel to the tool shaft and a cutting depth perpendicular to the tool shaft and parallel to the cutting insert, the axial distance between the first and second sets of cutting inserts is greater than the cutting depth of the first and second sets of cutting inserts;

the first and second sets of cutting inserts being staggered from each other by at least 10 degrees, the tool shaft includes an axial lubricant passage and at least one radial lubricant passage communicating with the axial lubricant passage and configured to deliver lubricant to each set of cutting inserts, and the tool shaft has an outer surface and a radius, and a distance between the cutting edge of each of the first set of cutting inserts and the tool shaft outer surface is greater than the tool shaft radius.

2. The tool of claim 1, wherein the first and second sets of cutting inserts are staggered from each other by at least 40 degrees.

3. The tool of claim 1, wherein the first and second sets of cutting inserts each include three cutting inserts and the first and second sets of cutting inserts are staggered from each other by about 60 degrees.

4. The tool of claim 1, further comprising a third set of set of radially spaced cutting inserts coupled to the tool shaft directly adjacent to the second set of inserts, opposite the first set of inserts, and spaced from the second set of inserts along the longitudinal axis.

5. The tool of claim 4, wherein the first, second, and third sets of cutting inserts are staggered from each other by at least 20 degrees.

6. The tool of claim 1, wherein the first set of cutting inserts each have a larger cutting depth than the second set of cutting inserts.

7. The tool of claim 1, wherein the first and second set of cutting inserts each have a positive rake angle.

8. An interpolated milling tool, comprising:
a tool shaft having a longitudinal axis;
a first set of radially spaced cutting inserts coupled to the tool shaft and disposed along a first longitudinal region of the longitudinal axis; and
a directly adjacent second set of radially spaced cutting inserts coupled to the tool shaft, disposed along a second longitudinal region of the longitudinal axis, and spaced from the first set of cutting inserts along the longitudinal axis an axial distance, the first and second regions non-overlapping along the longitudinal axis, each of the cutting inserts of the first and second sets having opposing sides tapering towards the tool shaft, a cutting edge parallel to the tool shaft, and a cutting depth perpendicular to the tool shaft and parallel to the cutting insert, and the axial distance between the first and second sets of cutting inserts is greater than the cutting depth of each of the first and second sets of cutting inserts, the tool shaft has an outer surface and a radius, and a distance between the cutting edge of each of the first set of cutting inserts and the tool shaft outer surface is greater than the tool shaft radius.

9. The tool of claim 8, wherein the first and second sets of cutting inserts are staggered from each other by at least 40 degrees.

10. The tool of claim 8, wherein the first and second sets of cutting inserts each include three cutting inserts and the first and second sets of cutting inserts are staggered from each other by about 60 degrees.

11. The tool of claim 8, further comprising a third set of set of radially spaced cutting inserts coupled to the tool shaft directly adjacent to the second set of inserts, opposite the first set of inserts, and spaced from the second set of inserts along the longitudinal axis, the third set of set of radially spaced cutting inserts disposed along a third longitudinal region of the longitudinal axis.

12. The tool of claim 11, wherein the first, second, and third sets of cutting inserts are staggered from each other by at least 20 degrees.

13. The tool of claim 8, wherein the first set of cutting inserts each have a larger cutting depth than the second set of cutting inserts.

14. An interpolated milling tool, comprising:
a tool shaft having a longitudinal axis;
a first set of radially spaced cutting inserts coupled to the tool shaft and disposed along a first longitudinal region of the longitudinal axis; and
a directly adjacent second set of radially spaced cutting inserts coupled to the tool shaft, disposed along a second longitudinal region of the longitudinal axis, and spaced from the first set of cutting inserts along the longitudinal axis an axial distance, the first and second regions non-overlapping along the longitudinal axis, and each of the cutting inserts of the first and second sets having a cutting edge having a radius of 0.005 to 0.05 mm and a cutting depth perpendicular to the tool shaft and parallel to the cutting insert, the first and second sets of cutting inserts each having a cutting edge parallel to the tool shaft and a cutting depth perpendicular to the tool shaft and parallel to the cutting insert, and the tool shaft has an outer surface and a radius, and a distance between the cutting edge of each of the first set of cutting inserts and the tool shaft outer surface is greater than the tool shaft radius.

15. The tool of claim 14, wherein the first and second sets of cutting inserts are staggered from each other by at least 40 degrees.

16. The tool of claim 14, wherein the first and second sets of cutting inserts each include three cutting inserts and the first and second sets of cutting inserts are staggered from each other by about 60 degrees.

17. The tool of claim 14, further comprising a third set of set of radially spaced cutting inserts coupled to the tool shaft directly adjacent to the second set of inserts, opposite the first set of inserts, and spaced from the second set of inserts along the longitudinal axis, the third set of set of radially spaced cutting inserts disposed along a third longitudinal region of the longitudinal axis.

18. The tool of claim 17, wherein the first, second, and third sets of cutting inserts are staggered from each other by at least 20 degrees.

* * * * *